United States Patent [19]

Kreighbaum et al.

[11] 4,148,908

[45] Apr. 10, 1979

[54] INDOLYL CYANOMETHYLPHENETHANOLAMINES

[75] Inventors: William E. Kreighbaum; William L. Matier; Herbert R. Roth, all of Evansville, Ind.

[73] Assignee: Mead Johnson & Company, Evansville, Ind.

[21] Appl. No.: 835,764

[22] Filed: Sep. 22, 1977

Related U.S. Application Data

[62] Division of Ser. No. 687,435, May 17, 1976, Pat. No. 4,055,658.

[51] Int. Cl.$^2$ .................. A61K 31/395; C07D 209/18
[52] U.S. Cl. ................................ 424/274; 260/326.15
[58] Field of Search .................... 260/326.15; 424/274

[56] References Cited

U.S. PATENT DOCUMENTS

3,859,305  1/1975  Posselt et al. .................. 260/326.15

FOREIGN PATENT DOCUMENTS

1211029  11/1970  United Kingdom ............... 260/326.15

*Primary Examiner*—Donald G. Daus
*Assistant Examiner*—D. B. Springer
*Attorney, Agent, or Firm*—Robert H. Uloth; Robert E. Carnahan

[57] ABSTRACT

Preparation of cyanomethylphenethanolamines useful as adrenergic stimulants is described. Preferred compounds such as 2-hydroxy-5-[1-hydroxy-2-[(1,1-dimethyl-2-phenylethyl)amino]ethyl]-benzeneacetonitrile are selective beta-adrenergic stimulants having relatively greater potency on respiratory smooth muscle than on cardiac muscle. Such compounds are particularly valuable in the treatment of bronchial conditions.

5 Claims, No Drawings

INDOLYL CYANOMETHYLPHENETHANOLAMINES

CROSS-REFERENCE TO RELATED APPLICATIONS

This application is a division of co-pending application Ser. No. 687,435 filed May 17, 1976, now U.S. Pat. No. 4,055,658 issued Oct. 25, 1977.

BACKGROUND OF THE INVENTION

This invention pertains to carbon compounds having drug and bio-affecting properties and is particularly concerned with novel cyanomethylphenethanolamines, to pharmaceutical preparations containing said phenethanolamines and to methods of producing and utilizing said phenethanolamines and compositions as adrenergic agents. Taken as a class, the cyanomethylphenethanolamines of this invention possess adrenergic stimulant properties and thus are variously suited as vasoconstrictors, mydriatic agents, nasal decongestants, cardiac stimulants, bronchodilators and peripheral vasodilators. The more preferred compounds are adrenergic beta-receptor stimulants having relatively greater selectivity for respiratory smooth muscle than cardiac muscle. These compounds are particularly useful as bronchodilators in patients susceptible to untoward cardiac and blood pressure conditions.

In the field of adrenergic agents, various phenethanolamine modifications have been studied in an effort to uncover more potent and selective adrenergic agents free of unwanted pharmacologic effects. By way of example, there can be mentioned such phenethanolamine modifications as meta-substituted-para-hydroxyphenethanolamines disclosed in the following patents.

(1) W. T. Comer, et al., U.S. Pat. No. 3,801,631 deals specifically with 2'-hydroxy-5'-[1-hydroxy-2-(2-methyl-1-phenyl-2-propylamino)ethyl]methanesulfonanilide.

(2) C. Kaiser, et al., U.S. Pat. No. 3,718,744 discloses phenethanolamines having meta-carboalkoxyamino substituents.

(3) L. H. C. Lunts, et al., U.S. Pat. No. 3,644,353 is concerned with phenethanolamines having various meta-substituents including hydroxyalkyl, hydroxyarylalkyl, alkoxycarbonyl, —CONHOH, —CONHNH$_2$, or an amido radical.

(4) D. Hartley, et al., U.S. Pat. No. 3,701,808 discloses phenethanolamines having sulfonamidoalkyl meta-substituents of the type exemplified by the compound "N-[5-2-tert.-butylamino-1-hydroxyethyl)-salicyl]methanesulfonamide" in addition to other phenethanolamines with meta-radicals such as ureido, H$_2$NCH$_2$— and R$_3$CONHCH$_2$— wherein R$_3$ is inter alia H, alkyl, OH, NH$_2$.

SUMMARY OF THE INVENTION

This invention is concerned with a new class of meta-substituted para-hydroxyphenethanolamines. More specifically, this invention pertains to cyanomethyl-p-hydroxyphenethanolamine bases characterized by Formula I and pharmaceutically acceptable acid addition salts thereof.

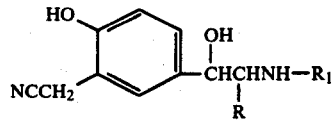

Formula I

In Formula I, R is hydrogen, methyl or ethyl and R$_1$ is hydrogen or a radical selected from the group consisting of straight or branched chain lower alkyl of 1 to 6 carbon atoms inclusive, straight or branched chain lower alkyl of 1 to 6 carbon atoms substituted by 3-indolyl, phenyl, phenoxy, substituted phenyl or substituted phenoxy wherein said phenyl or phenoxy substituent is hydroxy, methoxy, or halogen (i.e. chlorine, bromine, iodine, fluorine).

Contemplated sub-classes of compounds embodied in general Formula I are:

those wherein R is hydrogen and R$_1$ is as defined above;
those wherein R is hydrogen, methyl or ethyl and R$_1$ is hydrogen, methyl or ethyl;
those wherein R is hydrogen and R$_1$ is hydrogen, methyl or ethyl;
those wherein R is hydrogen and R$_1$ is straight or branched chain alkyl of 3 to 6 carbon atoms inclusive;
those wherein R is hydrogen, methyl or ethyl and R$_1$ is straight or branched chain alkyl of 3 to 6 carbon atoms;
those wherein R is hydrogen and R$_1$ is straight or branched chain alkyl of 1 to 6 carbon atoms substituted by phenyl;
those wherein R is hydrogen, methyl or ethyl and R$_1$ is straight or branched chain alkyl of 1 to 6 carbon atoms substituted by phenyl;
those wherein R is hydrogen and R$_1$ is straight or branched chain alkyl of 1 to 6 carbon atoms substituted by phenoxy;
those wherein R is hydrogen, methyl or ethyl and R$_1$ is straight or branched chain alkyl of 1 to 6 carbon atoms substituted by phenoxy;
those wherein R is hydrogen, methyl or ethyl and R$_1$ is straight or branched chain alkyl of 1 to 6 carbon atoms substituted by substituted phenyl wherein said substituent is hydroxy, methoxy, or halogen;
those wherein R is hydrogen and R$_1$ is straight or branched chain alkyl of 1 to 6 carbon atoms substituted by substituted phenyl wherein said phenyl substituent is hydroxy, methoxy, or halogen;
those wherein R is hydrogen, methyl or ethyl and R$_1$ is straight or branched chain alkyl of 1 to 6 carbon atoms substituted by substituted phenoxy wherein said phenoxy substituent is hydroxy, methoxy, or halogen;
those wherein R is hydrogen and R$_1$ is straight or branched chain alkyl of 1 to 6 carbon atoms substituted by substituted phenoxy wherein said phenoxy substituent is hydroxy, methoxy, or halogen;
those wherein R is hydrogen and R$_1$ is straight or branched chain alkyl of 1 to 6 carbon atoms substituted by 3-indolyl;

those wherein R is hydrogen and $R_1$ is selected from the group of radicals consisting of isopropyl, t-butyl, phenyl-t-butyl, p-hydroxyphenyl-t-butyl, (3-indolyl)isopropyl and (3-indolyl)-t-butyl.

It will be apparent to those skilled in the art that the carbinol carbon atom of the compounds of the instant invention is an asymmetric carbon atom. Thus, there exists for each structure at least one racemate consisting of a pair of enantiomorphs which are equally the same in their chemical and physical properties but which differ in the direction they will rotate the plane of polarized light. Resolution of racemates into optically active isomers can be carried out by conventional methods familiar to those skilled in the art, for example, by salt formation with an optically active acid, followed by fractional crystallization.

It is to be understood that the term "pharmaceutically acceptable acid addition salt" used herein denotes a combination of a phenethanolamine base characterized by Formula I with a relatively non-toxic inorganic or organic acid. Illustrative of suitable acids which may be used are sulfuric, hydrochloric, phosphoric, hydrobromic, hydroiodic, sulfamic, methanesulfonic, benzenesulfonic, para-toluene sulfonic, acetic, lactic, succinic, maleic, mucic tartaric, citric, gluconic, benzoic, cinnamic, isethionic, fumaric, and related acids. The phenethanolamine bases of the present invention are converted to the acid addition salts by interaction of the base with an acid either in an aqueous or non-aqueous medium. In a similar manner, treatment of the acid addition salts with an aqueous base solution, e.g., alkali metal hydroxides, alkali metal carbonates, result in a regeneration of the free base form. The bases thus regenerated may be reconverted to the same or a different acid addition salt.

The present invention provides a process for preparation of compounds characterized by Formula I which comprises reducing a ketone of general Formula II wherein R and $R_1$ are as defined by Formula I.

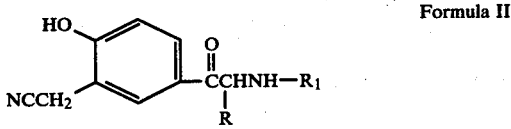

Formula II

Reduction is carried out by conventional catalytic and chemical methods that do not appreciably affect the nitrile radical. Mild reducing agents such as sodium borohydride, diborane, disiamylborane or lithium tri-t-butoxyaluminohydride are preferred with the reduction carried out in relatively reaction inert solvents such as ethanol or isopropanol. The amino ketone of Formula II may be prepared by condensation of an amine of the general formula $NH_2R_1$ wherein $R_1$ is as defined by Formula I with a cyanomethylphenacyl bromide of Formula III wherein R is as defined by Formula I in a reaction inert solvent.

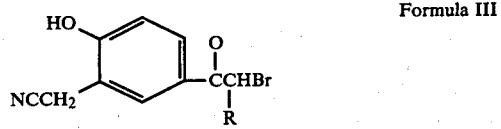

Formula III

Cyanomethylphenacyl bromides of Formula III may be prepared by brominating 5-acetyl-2-hydroxyphenylacetonitriles of Formula IV wherein R is as defined by Formula I with bromine in an inert reaction solvent such as tetrahydrofuran, chloroform, ethylacetate and the like or with other suitable brominating agents such as trimethylphenylammonium tribromide.

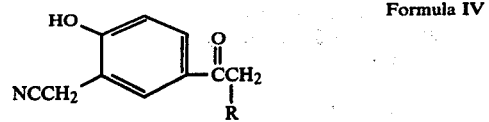

Formula IV

The 5-acetyl-2-hydroxyphenylacetonitriles of Formula IV are obtained by reacting the corresponding 3-chloromethyl-4-hydroxyacetophenone with sodium cyanide in a reaction inert solvent such as dimethylsulfoxide.

As stated hereinabove, the compounds of Formula I are adrenergic stimulants. In particular, the compounds of Formula I wherein R and $R_1$ are independently selected from the group consisting of hydrogen, methyl or ethyl tend to be predominantly alpha-adrenergic stimulants and thus are useful as vasoconstrictors, mydriatic agents, nasodecongenstants, and cardiac stimulants for use in cardiac shock. Those substances of Formula I wherein $R_1$ is straight or branched chain lower alkyl of 3 to 6 carbon atoms inclusive, straight or branched chain lower alkyl of 1 to 6 carbon atoms substituted by 3-indolyl, phenyl, phenoxy, substituted phenyl or substituted phenoxy wherein said phenyl or phenoxy substituent is hydroxy, methoxy or halogen are primarily beta-adrenergic stimulants and thus are useful as bronchodilating agents and peripheral vasodilators. The most preferred compounds of the instant invention have selective beta-adrenergic stimulant activity with relatively greater effect on respiratory smooth muscle than on cardiac muscle and, accordingly, are particularly useful as bronchodilating agents in that they dilate bronchi without undue cardiac effects.

This pharmacological specificity of action can be demonstrated in standard in vitro and in vivo pharmacological tests. Two in vitro test systems particularly useful in determining selective beta stimulant activity are: (1) effect on spontaneous tone of guinea pig tracheal chain preparations as a measure of relaxant effect on airway smooth muscle, and (2) effect on force and rate of spontaneously beating right atria of the guinea pig as a measure of beta-stimulant effect on cardiac muscle. If a beta-adrenergic agent exerts an effect on spontaneous tone of guinea pig trachea at a concentration lower than is required to affect heart force and rate, there is a positive separation ratio and the agent is considered to have bronchodilator activity with minimal cardiac stimulation. Thus, a comparison of the test agent with standard beta-stimulants such as isoproterenol or other beta-adrenergic agents can be made and relative bronchial selectivity determined.

A preferred embodiment of this invention, "2-hydroxy-5-[1-hydroxy-2-[(1,1-dimethyl-2-phenylethyl)amino]ethyl]benzeneacetonitrile hydrochloride" provides a 50% decrease in the spontaneous tone of the guinea pig trachea at an effective bath concentration (EC) of 0.0055 ±0.0008 mcg./ml. while increasing both the rate and force of guinea pig right atria at an $EC_{50}$ of 0.33 ±0.1 mcg./ml. and 0.16 ±0.028 mcg./ml., respectively.

Suitable in vivo models for demonstrating the selective bronchodilator activity of the compounds of the instant invention employ anesthetized rats or dogs. In the rat, transient bronchoconstriction is induced with a short-lasting intravenous (i.v.) infusion of methacholine to obtain a control value and at various times thereafter following intraduodenal (i.d.) administration of the test drug. Doses of test drug blocking methacholine induced bronchoconstriction are determined. In the dog, sustained bronchoconstriction is induced by continuous i.v. infusion of serotonin and doses of test drug necessary to reverse the bronchoconstriction are determined. In both animal models, measurements of cardiovascular effects from test drug is made simultaneously with the determination of the dose reversing bronchoconstriction. These in vivo comparisons are considered particularly significant since the bronchoconstriction induced resembles asthma and intraduodenal drug dosing of the anesthetized animal (i.e., rat) is similar to oral administration to a conscious animal. In the rat, 2-hydroxy-5-[1-hydroxy-2-[(1,1-dimethyl-2-phenylethyl)amino]ethyl]-benzeneacetonitrile hydrochloride at a dose of 0.5 mg./kg. and 2.0 mg./kg. of body weight antagonizes methacholine-induced bronchoconstriction by 33.5 ±5.2% and 72.3 ±4.0%, respectively. In the dog, 2-hydroxy-5-[1-hydroxy-2-[(1,1-dimethyl-2-phenylethyl)amino]ethyl]benzeneacetonitrile hydrochloride reduces serotonin-increase pulmonary airway resistance by 49.7 ±13.4% at 0.125 mg./kg. body weight and by 96.7 ±12.3% at 0.5 mg./kg. body weight. The aforementioned bronchodilating effects are obtained in the rat and dog without appreciably affecting heart rate of either species.

Another feature of the invention provides pharmaceutical compositions having bronchodilating activity in dosage unit form comprising a phenethanolamine of Formula I and a pharmaceutically acceptable acid addition salt thereof. While the instant compounds may be administered to mammals for bronchodilating purposes as individual therapeutic agents, they are generally administered with a pharmaceutical carrier selected on the basis of the chosen route of administration and standard pharmaceutical practice. For example, they may be combined with various pharmaceutically acceptable inert carriers in the form of tablets, capsules, lozenges, troches, powders, aerosol sprays, aqueous suspensions or solutions, injectible solutions, elixirs, syrups and the like. Such carriers include solid diluents, or fillers, sterile aqueous media and various non-toxic organic solvents.

The particular carrier selected and proportion of active ingredient to carrier is determined to some extent upon the chosen route of administration and the needs of standard pharmaceutical practice. For example, when the instant compounds are administered orally in tablet form, excipients such as lactose, sodium citrate, calcium carbonate, and dicalcium phosphate may be used. Various disintegrating agents such as starch, alginic acids together with lubricating agents such as magnesium stearate, sodium lauryl sulfate and talc, may also be used in producing tablets for the oral administration of the instant compounds. For oral administration in capsule form, lactose and high molecular weight polyethylene glycols are among the preferred materials for use as pharmaceutically acceptable carriers. Where aqueous suspensions are to be used for oral administration, the compounds of this invention may be combined with emulsifying or suspending agents. Diluents such as ethanol, propylene glycol, glycerin, and their combinations may be employed as well as other materials.

For purposes of parenteral administration, solutions or suspensions of the Formula I compounds in sesame or peanut oil or in aqueous propylene glycol solutions can be employed, as well as sterile aqueous solutions of the soluble pharmaceutically acceptable acid addition salts described hereinabove. These particular solutions are especially suited for intramuscular and subcutaneous injection purposes. The aqueous solutions, including those of the acid addition salts dissolved in pure distilled water, are also useful for intravenous injection or inhalation purposes provided their pH is properly adjusted beforehand.

The instant compounds may be administered to subjects suffering from bronchoconstriction by means of aerosol sprays or inhalators which permit the active compound to come into direct contact with the constricted areas of the tissues of the subject such as the insufflation device described in U.S. Pat. No. 3,634,582.

According to a further feature of the invention, there is provided a method for effecting bronchodilation in a mammal, including man, in need of such treatment which comprises administering orally, parenterally or by inhalation to said mammal an effective bronchodilator amount ranging from 2 to 2000 mcg./kg. of body weight of a phenethanolamine characterized by Formula I or a pharmaceutically acceptable acid addition salt thereof.

Although the use of the present invention is directed toward the treatment of mammals in general, the preferred subject is human and the efficacious dose for human therapy will be determined by the physician in accordance with accepted clinical practice. Generally, small doses of the compounds of Formula I will be administered initially, with a gradual increase in the dosage until the optimum level is determined. In most instances, it will be found that when the instant compositions are administered orally, larger quantities of the active ingredient will be required to produce the same bronchodilator effect as produced by a small quantity administered parenterally.

The invention is illustrated but not limited by the following examples.

EXAMPLE 1

2-Hydroxy-5-[1-hydroxy-2-[(1,1-dimethyl-2-phenylethyl)amino]ethyl]benzeneacetonitrile Hydrochloride (a) 5-Acetyl-2-hydroxyphenylacetonitrile—To a stirred suspension of sodium cyanide (32.2 g., 0.66 mole) in 150 ml. of dimethylsulfoxide is added 3-chloromethyl-4-hydroxyacetophenone (55.3 g., 0.3 mole) with stirring under a nitrogen atmosphere. The mixture is stirred for a period of 16 hr. at room temperature, poured with stirring into 800 ml. of water and filtered from a small amount of insoluble flocculent material. The filtrate is acidified with concentrated hydrochloric acid and insolubles collected, washed with water and dried to provide 41.3 g. (79%) of 5-acetyl-2-hydroxyphenylacetonitrile, m.p. 154°–168° C. Crystallization of this material from acetonitrile affords 5-acetyl-2-hydroxyphenylacetonitrile, m.p. 180°–185° C.

(b) 5-Bromoacetyl-2-hydroxyphenylacetonitrile—To 5-acetyl-2-hydroxyphenylacetonitrile (3.5 g., 0.02 mole) in 100 ml. of tetrahydrofuran is added trimethylphenylammonium tribromide (7.6 g., 0.02 mole) portionwise over a 15 min. period with stirring. After stirring for an additional 18 hrs. at 25° C., the reaction mixture is concentrated to dryness under reduced pressure. Trituration of residual material with water affords 5.0 g. of brominated product, m.p. 187°–191° C. (dec.). Crystallization of this material from isopropanol affords 5-bromoacetyl-2-hydroxyphenylacetonitrile, m.p. 196°–198° C. (dec.).

(c) 5-[N-(1,1-dimethyl-2-phenethyl)glycyl]-2-hydroxyphenylacetonitrile hydrochloride—A mixture of 5-bromoacetyl-2-hydroxyphenylacetonitrile (15.2 g., 0.06 mole) and phenyl-t-butylamine (20 g., 0.132 mole) in 600 ml. of methylene chloride is refluxed for a period of 14 hrs. and then concentrated under reduced pressure. The residue thus obtained is taken up in 100 ml. of butanone, acidified to pH 2 with 5 ethanolic 5N hydrogen chloride and concentrated to a residue. Trituration of this residual material with butanone affords 23 g. of solid which is further triturated with water yielding 10.5 g. of 5-[N-(1,1-dimethyl-2-phenylethyl)glycyl]-2-hydroxyphenylacetonitrile hydrochloride, m.p. 206°–210° C. (dec.).

(d) Reduction of 5-[N-(1,1-dimethyl-2-phenylethyl)glycyl]-2-hydroxyphenylacetonitrile hydrochloride—Sodium borohydride (5.0 g., 0.136 mole) is added portionwise over 30 min. to a stirred solution of 5-[N-(1,1-dimethyl-2-phenylethyl)glycyl]-2-hydroxyphenylacetonitrile hydrochloride (10.5 g., 0.03 mole) in 300 ml. of ethanol at about 40° C. After stirring for 4 days at 25° C., the mixture is concentrated under reduced pressure and residual material triturated with 250 ml. of water forming a gummy precipitate. The mixture is adjusted to pH 8–8.5 with acetic acid and the aqueous fraction decanted from the gummy solid which is taken up in acetone, acidified with ethanolic hydrogen chloride, filtered and concentrated under reduced pressure. Residual material triturated with isopropanol provides 6.5 g. of 2-hydroxy-5-[1-hydroxy-2-[(1,1-dimethyl-2-phenylethyl)amino]ethyl]-benzeneacetonitrile hydrochloride, m.p. 187°–188° C. (dec.). The product, 2-hydroxy-5-[1-hydroxy-2[(1,1-dimethyl-2-phenylethyl)amino]ethyl]benzeneacetonitrile hydrochloride, is obtained analytically pure by crystallization from acetonitrile-methanol, m.p. 184.0°–185.0° C. (dec.) (corr.).

Analysis—Calcd. for $C_{20}H_{24}N_2O_2 \cdot HCl$ (percent): C, 66.56; H, 6.98; N, 7.76. Found (percent): C, 66.59; H, 6.95; N, 7.59.

Treating 2-hydroxy-5-[1-hydroxy-2-[(1,1-dimethyl-2-phenethyl)-amino]ethyl]benzeneacetonitrile hydrochloride (0.1 mole) in ethanol or aqueous solution with 0.1 mole of an alkaline base such as sodium hydroxide or sodium methoxide followed by concentration of the neutralized mixture provides 2-hydroxy-5-[1-hydroxy-2-[(1,1-dimethyl-2-phenethyl)amino]ethyl]benzeneacetonitrile free base.

EXAMPLE 2

2-Hydroxy-5-[1-hydroxy-2-(isopropylamino)ethyl]benzeneacetonitrile

The procedure of Example 1(c) is repeated with substitution of an equimolar amount of isopropylamine for phenyl-t-butylamine in that example. The resulting aminoketone, 5-[N-(isopropylamino)glycyl]-2-hydroxyphenylacetonitrile, is reduced according to the procedure of Example 1(d) to yield 2-hydroxy-5-[1-hydroxy-2-(isopropylamino)ethyl]benzeneacetonitrile.

EXAMPLE 3

2-Hydroxy-5-[1-hydroxy-2-(t-butylamino)ethyl]benzeneacetonitrile

The procedure of Example 1(c) is repeated with substitution of an equimolar amount of t-butylamine for phenyl-t-butylamine in that example. The resulting aminoketone, 5-[N-(t-butylamino)glycyl]-2-hydroxyphenylacetonitrile is reduced according to the procedure of Example 1(d) to yield 2-hydroxy-5-[1-hydroxy-2-(t-butylamino)ethyl]-benzeneacetonitrile.

EXAMPLE 4

2-Hydroxy-5-[1-hydroxy-2-[(1,1-dimethyl-2-p-hydroxyphenylethyl)amino]ethyl]benzeneacetonitrile The procedure of Example 1(c) is repeated with substitution of an equimolar amount of p-hydroxyphenyl-t-butylamine for phenyl-t-butylamine in that example. The resulting aminoketone, 5-[N-(1,1-dimethyl-2-p-hydroxyphenylethyl)glycyl]-2-hydroxyphenylacetonitrile, is reduced according to the procedure of Example 1(d) to yield 2-hydroxy-5-[1-hydroxy-2-[(1,1-dimethyl-2-p-hydroxyphenylethyl)amino]ethyl]benzeneacetonitrile.

EXAMPLE 5–15

Further exemplification of cyanomethylphenethanolamines of the present invention is listed below in Table I. The cyanomethyl products are prepared by reducing, according to the procedure of Example 1(d), the corresponding aminoketones which are obtained in a manner analogous to Example 1(c).

TABLE I
ADDITIONAL CYANOMETHYLPHENETHANOLAMINES $$\text{NCCH}_2\text{-C}_6\text{H}_3(\text{OH})\text{-CHOH-CH}_2\text{-N}(R)\text{-R}_1$$

| Example No. | R | $R_1$ |
|---|---|---|
| 5 | H | H |
| 6 | H | $CH_3$ |
| 7 | H | $C_6H_5OCH_2CH_2-$ |
| 8 | H | $C_6H_5OCHCH_2-$<br>$\quad\mid$<br>$\quad CH_3$ |
| 9 | H | $p\text{-}HOC_6H_4OCH_2CH-$<br>$\quad\mid$<br>$\quad CH_3$ |
| 10 | H | $p\text{-}CH_3OC_6H_4OCH_2CH-$<br>$\quad\mid$<br>$\quad CH_3$ |
| 11 | $CH_3$ | H |
| 12 | $CH_3$ | $(CH_3)_3C-$ |
| 13 | $CH_3$ | $\quad CH_3$<br>$\quad\mid$<br>$C_6H_5CH_2C-$<br>$\quad\mid$<br>$\quad CH_3$ |
| 14 | H | $\quad CH_3$<br>$\quad\mid$<br>$p\text{-}ClC_6H_4CH_2C-$<br>$\quad\mid$<br>$\quad CH_3$ |
| 15 | H | $\quad CH_3$<br>$\quad\mid$<br>$m\text{-}BrC_6H_4CH_2C-$<br>$\quad\mid$<br>$\quad CH_3$ |

EXAMPLE 16

2-Hydroxy-5-[1-hydroxy-2-[1-(3-indolyl)-2-propylamino]ethyl]benzeneacetonitrile

Reduction of 5-[N-(3-indolylisopropyl)glycyl]-2-hydroxyphenylacetonitrile according to procedure of Example 1(d) yields 2-hydroxy-5-[1-hydroxy-2-[1-(3-indolyl)-2-propylamino]ethyl]benzeneacetonitrile characterized by the formula

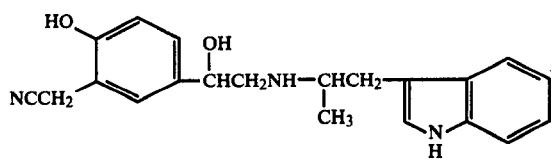

EXAMPLE 17

2-Hydroxy-5-[1-hydroxy-2-[(1,1-dimethyl-2-2-(3-indolyl)ethyl)amino]ethyl]benzeneacetonitrile Reduction of 5-[N-[1,1-dimethyl-2-(3-indolyl)ethyl)]-glycyl]-2-hydroxyphenylacetonitrile, according to procedure of Example 1(d) yields 2-hydroxy-5-[1-hydroxy-2-[(1,1-dimethyl-2-(3-indolyl)ethyl)amino]ethyl]benzeneacetonitrile characterized by the formula

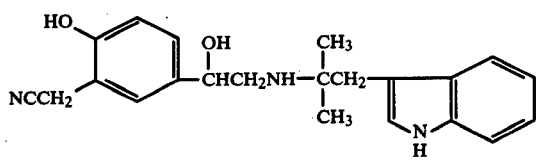

EXAMPLE 18

Capsules

A blend is prepared containing the following ingredients. 2-Hydroxy-5-[1-hydroxy-2-[(1,1-dimethyl-2-phenylethyl)amino]ethyl]benzeneacetonitrile hydrochloride and lactose q.s. to provide capsules containing 0.2, 0.5, 1.0, 2.0, 4.0, 8.0, 16 and 32 mg. of active ingredient per capsule. The compositions are filled into conventional hard gelatin capsules in the amount of 120 or 300 mg. per capsule.

EXAMPLE 19

Tablets

The following ingredients when thoroughly blended in the dry state in a twin-shell blender provide a composition suitable for tableting in a standard tablet press using a ¼-inch concave die. The batch size is sufficient for 1,000 tablets containing 0.2 mg. of active ingredient per tablet.

| 2-Hydroxy-5-[1-hydroxy-2-[(1,1-dimethyl-2-phenylethyl)amino]ethyl]benzene-acetonitrile hydrochloride | 0.22 g. |
|---|---|
| Lactose | 77.28 g. |
| Corn starch | 2.0 g. |
| Crystalline cellulose | 20.0 g. |
| Magnesium stearate | 0.5 g. |

The batch size is sufficient for 1,000 tablets containing 0.2 mg. of active ingredient per tablet.

EXAMPLE 20

Solutions for Nebulization

The following ingredients are used to prepare a solution which is clarified by filtration and then filled into 10 ml. amber glass bottles.

| Ingredients | Grams |
|---|---|
| 2-hydroxy-5-[1-hydroxy-2-[(1,1-dimethyl-2-phenylethyl)amino]ethyl]benezene-acetonitrile hydrochloride | 11.1 |
| Sodium bisulfite | 2.00 |
| Chlorobutanol, U.S.P. | 5.00 |
| Propylene glycol | 50.00 |
| Sodium saccharin | 1.00 |
| Citric acid, anhydrous | 1.92 |
| Purified water, q.s. 1,000 ml. | |
| Sodium hydroxide, q.s. pH 3.75 | |

The foregoing solution is suitable for administration in conventional nebulization equipment adapted for administration of drugs by inhalation. This solution contains 1.11% by weight of the hydrochloride salt equivalent to 1% by weight of the active ingredient free base 2-hydroxy-5-[1-hydroxy-2-[(1,1-dimethyl-2-phenylethyl)amino]-ethyl]benzeneacetonitrile. The concentration of active ingredients may be varied to provide similar solutions containing an amount of the hydrochloride salt equivalents to from 0.02 to 2% by weight of the active ingredient base.

What is claimed is:

1. A compound selected from the group of phenethanolamines of the formula

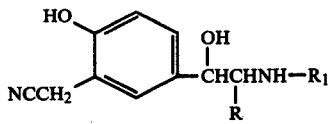

or a pharmaceutically acceptable acid addition salt thereof wherein

R is hydrogen, methyl or ethyl;

$R_1$ is straight or branched chain lower alkyl of 1 to 6 carbon atoms substituted by 3-indolyl.

2. The compound of claim 1 which is 2-hydroxy-5-[1-hydroxy-2-[1-(3-indolyl)-2-propylamino]ethyl]benzeneacetonitrile.

3. The compound of claim 1 which is 2-hydroxy-5-[1-hydroxy-2-[(1,1-dimethyl-2-(3-indolylethyl)amino]ethyl]benzeneacetonitrile.

4. A pharmaceutical composition in dosage unit form having a pharmaceutical carrier and an effective bronchodilating amount of a compound selected from the group of phenethanolamines of the formula

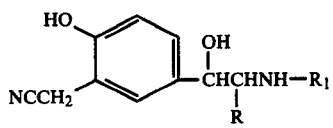

or a pharmaceutically acceptable acid addition salt thereof wherein

R is hydrogen, methyl or ethyl;

$R_1$ is straight or branched chain lower alkyl of 1 to 6 carbon atoms substituted by 3-indolyl.

5. A method for effecting bronchodilation in a mammal in need of such treatment which comprises the step of administering to said mammal an effective bronchodilator amount of a compound selected from the group of phenethanolamines of the formula

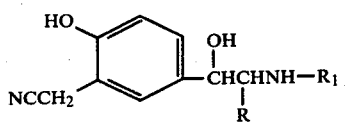

or a pharmaceutically acceptable acid addition salt thereof wherein
R is hydrogen, methyl or ethyl;
$R_1$ is straight or branched chain lower alkyl of 1 to 6 carbon atoms substituted by 3-indolyl.

* * * * *